United States Patent [19]
Puchinger et al.

[11] 4,225,671
[45] Sep. 30, 1980

[54] PROCESS FOR THE IN-VITRO BIOSYNTHESIS OF HORMONES, ESPECIALLY INSULIN

[75] Inventors: Herwig Puchinger, Neu Isenburg; Ulrich Mueller, Ruesselsheim; Manfred Sernetz, Krofdorf, all of Fed. Rep. of Germany

[73] Assignee: Battelle-Institut e.V., Frankfurt am Main, Fed. Rep. of Germany

[21] Appl. No.: 914,138

[22] Filed: Jun. 9, 1978

[30] Foreign Application Priority Data

Jun. 10, 1977 [DE] Fed. Rep. of Germany ....... 2726313

[51] Int. Cl.$^2$ ............................................. C12P 21/04
[52] U.S. Cl. ...................................... 435/71; 435/240; 435/285; 435/813
[58] Field of Search ...................... 195/1, 127, 142, 1.7, 195/1.8; 435/71, 240, 285

[56] References Cited

U.S. PATENT DOCUMENTS

| | | | |
|---|---|---|---|
| 3,821,087 | 6/1974 | Knazek et al. | 195/127 |
| 3,873,423 | 3/1975 | Munder et al. | 195/127 |
| 3,948,732 | 4/1976 | Haddad et al. | 195/142 |
| 4,082,613 | 4/1978 | Thirumalachar et al. | 195/1 |

*Primary Examiner*—Alvin E. Tanenholtz
*Attorney, Agent, or Firm*—Fisher, Christen & Sabol

[57] ABSTRACT

Process for the in-vitro biosynthesis of hormones, especially of insulin, by in-vitro conservation or in-vitro propagation of cells from organs and tissues of animal or human origin under suitable cell growth and cell conservation conditions and isolation of the substance formed in a known manner from the culture medium or by processing of the cells. The hormone-producing cells are propagated or conserved in one or more cell culture spaces separated by semipermeable flat membranes of at least one culture medium space.

12 Claims, 6 Drawing Figures

PROCESS FOR THE IN-VITRO BIOSYNTHESIS OF HORMONES, ESPECIALLY INSULIN

BACKGROUND OF THIS INVENTION

1. Field of This Invention

This invention relates to a process for the in-vitro biosynthesis of hormones, especially of insulin, by in-vitro conservation or in-vitro propagation of cells from organs and tissues of animal or human origin under suitable conditions for cell growth and cell conservation, and isolation of the formed substances in a known manner from the culture medium or by the processing of the cells.

2. Prior Art

High value natural substances of animal or human origin, for example, insulin or other hormones, nowdays fulfill important tasks in medicine and biochemistry. Here one is mostly dealing with substances which heretofor could not be produced chemically or could be produced only with the utmost difficulty. At the present time, the tissue or body fluids of animals serve almost exclusively as raw materials for the production of such expensive substances. Since the product that is to be obtained is often contained in only a small portion of the cells of the tissues to be processed, there is always a high ballast (amount) of unspecific, unwanted material. In the future, additional problems will be present in the procurement of the raw material.

Furthermore, it will be absolutely necessary for reasons of the specificity of the species to reach back, at least partially, for materials of human origin since corresponding products obtained from animal material have too low of an effectiveness (efficacy) or no effectiveness at all. As far as one is dealing here with tissues, the required material is only available in insufficient quantities and mostly in unsatisfactory condition. Therefore, it is still unavoidable in most cases to escape the need to resort to the use of animal material.

Up to this point in time, suitable and generally applicable processes for cultures for mass propagation of cells are still lacking. One must consider that the cultivated cells adapt themselves to the empirically composed culture medium and must build up at least a microenvironment with relatively favorable growth conditions. In the case of the "surface" process such is possible in principle, however, the yield of cells is low since the cells have only two dimensional growth. In the case of the "suspension" process, such microenvironment is constantly disturbed by the changing contact (interface) with the culture medium. In addition, such process could be used hitherto only for a few type of cells.

German OS No. 2,431,450 teaches a process for the in-vitro propagation or in-vitro conservation of cells which is carried out using hollow fiber diaphragms. Such process, however, has the disadvantage that any build-up (scale up) of a technical (industrial) system is not practical.

The known culture processes furthermore mostly lead to "de-differentiation" and thus to a more or less quick loss of the specific synthesis functions of the cells. The de-differentiation, however, is not a process inherent in cells—it is caused in the first place by insufficient culture conditions.

Another disadvantage of the known culture processes is the high costs for the culture medium, which are caused by having to add up to 90 percent of blood serum. Customarily 10 percent of blood serum must be added to the culture medium.

BROAD DESCRIPTION OF THIS INVENTION

An object of this invention is to eliminate or overcome the disadvantages of the known culture processes. Another object of this invention is to provide a process with which animal and human cells can be conserved or multiplied in-vitro in an economic manner. A further object of this invention is to provide a process wherein the addition of blood serum in the space of the culture medium is reduced to less than 0.5 percent. Other objects and advantages of this invention are set out herein or are obvious herefrom to one ordinarily skilled in the art.

The advantages and objects of this invention are achieved by the process of this invention.

Applicants have found that these objects can be achieved in a technically progressive manner whenever hormone-producing cells, according to this invention, are propagated or conserved in one or more cell-culture spaces, separated from at least one culture-medium space by semi-permeable flat membranes.

This invention involves a process for the in-vitro biosynthesis of hormones, especially of insulin. The process includes the in-vitro propagation of cells from organs and tissues of animal or human origin under suitable cell growth and cell conservation conditions and isolating the substance formed in a known manner from the culture medium or by processing of the cells. The hormone-producing cells are propagated or conserved in one or more cell culture spaces separated by semipermeable flat membranes of at least one culture medium space.

Preferably the culture medium is in a circulation system and is repeatedly conducted into the culture medium spaces—the circulation system includes a culture medium supply container, assurance and control arrangements and possibly an oxygenator. Preferably the culture medium, in a continuous flow-through system, is conducted once into the culture medium spaces in order to obtain the substances released via the membranes. Preferably the cell culture spaces are separated by semipermeable flat membranes on top and below from culture medium spaces. Also, preferably the cell culture spaces are separated by semipermeable flat membranes on top from a culture medium space and below from a gas space.

For carrying out the process of this invention, flat membranes are used for the cell-culture system. Preferably the flat membranes are permeable to molecules having a molecular weight up to of 100,000, but are impermeable to the cells. The flat membranes can be produced from any kind of material. The material used, however, must be very compatible with the cells and cannot contain any components which are toxic to the cells. The material can be, for example, cellulose, cellulose derivatives, polypeptides, polyamides, polysulfone or polyacrylic nitrile. The thickness of each flat membrane should be within the range of 10 to 150 $\mu$m, preferably 30 to 100 $\mu$m. The membranes, however, must be sufficiently thick so as not to break or crack (through), but sufficiently thin to make possible the desired exchange of substances. The distance between the installed flat membranes in the cell culture system is preferably 2 mm.

The cells are cultured in a suitable culture medium under cell-growth or cell-conservation conditions of pH and temperature. A corresponding culture medium is also used in the cell-culture space. Suitable culture media are known and can be used in the process of this invention. Such culture media generally is composed of essential amino acids, carbohydrates, vitamins, mineral acids and blood serum. In order to prevent undesirable growth of bacteria and fungi, suitable bactericides and fungicides respectively can be added. The pH value of the culture medium is adjusted preferably to between 6.8 and 8.0. The gas mixtures used are air or some other mixture of nitrogen and oxygen, preferably to which a small quantity of carbon dioxide, for example, at an order of magnitude of 2 to 5 percent, is added. The carbon dioxide serves to create a carbonate buffer in the culture medium. The carbonate buffer contributes to maintaining the pH value of the culture medium in the desired shape. Beside the carbonate buffer, other suitable buffer systems, for example "HEPES"-buffer, can also be used in the culture medium. The suitable temperature can easily be found at which optimum cell conservation takes place.

Suitable cells for the in-vitro biosynthesis of insulin, according to the process of this invention, include insulin-producing B-cells from the pancreas of animal or human origin, inclusive of normal or abnormal types of cells, for example, from pancreas tumors. But other cells of organs and tissue of animal and human origin, inclusive of normal and abnormal types of cells, which have a specific synthesis function for certain hormones, can also be multiplied or conserved according to the process of this invention.

DETAILED DESCRIPTION OF THIS INVENTION

Further characteristics, advantages and possibilities of application of this invention become clear from the following disclosure on the basis of the Figures and specific embodiments.

In the drawings (shown in schematic simplification):

Figure 1:
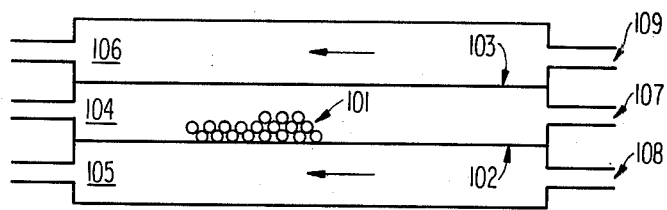
FIG. 1 is the functional pattern of the plate membrane system used according to this invention.

FIG. 1 shows the basic pattern of the plate membrane system used according to this invention. Cells 101 innoculated into the plate membrane system are cultivated between two tightened, semi-permeable, flat membranes 102 and 103 in cell-culture space 104 in a suitable culture medium. The innoculation of cell suspension 104 is done via inlet 107. Cell culture space 104 is separated by semipermeable flat membranes 102 and 103 either from both culture medium spaces 105 and 106, or on top from culture medium space 106 and below from gas space 105. Whenever 105 is a gas space, membrane 102 is gas-permeable but not water permeable. Above inlets 108 or 109, the culture-medium space is brought into contact with a suitable culture medium and is continuously perfused when carrying out the process using a gas space, then a suitable gas mixture is introduced via the inlet 108.

Figure 2:
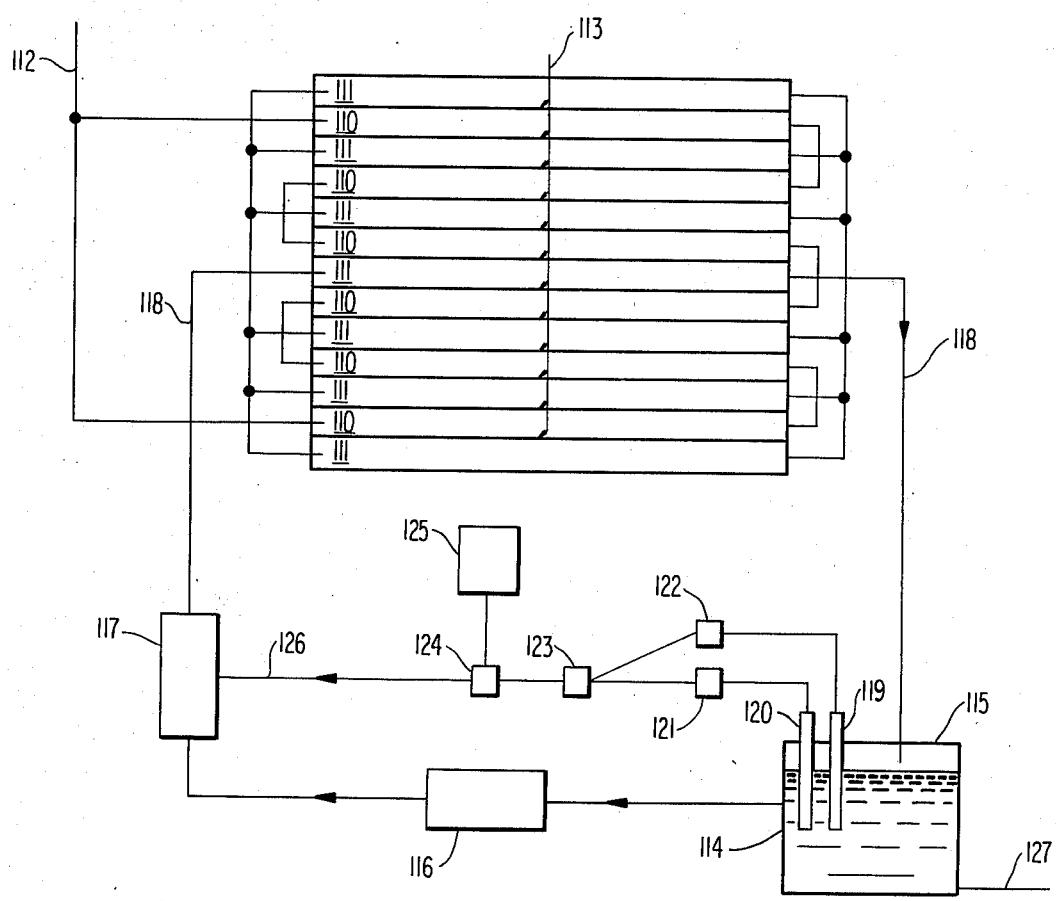
FIG. 2 is the functional pattern for the circulation process where two culture medium spaces are always adjacent to one cell culture space.

The functional pattern for the circulation process where cell culture spaces 110 are always separated above and below from culture medium spaces 111 is shown in FIG. 2. When carrying out the process of this invention the cells are innoculated via inlet 112 under aseptic conditions into the cell culture system, at the same time, preferably several layers of semipermeable flat membranes 113 are superimposed in such a way that one cell culture space 110 always alternates with one culture medium space 111, which are all accessible laterally, separated and are not interconnected. Culture medium 114 is continuously transported from supply tank 115 via pump 116 through oxygenator 117, supply line 118 and culture medium space 111 of the cell-culture system and then back to supply tank (bottle) 115. Supply tank 115 is equipped with measuring devices 119 and 120 in order to make pH and oxygen measurements with instrumental 121 and 122. Instruments 121 and 122 are connected with control device 123 in order to control (supply) a suitable gas mixture from tank 125 into oxygenator 117 via valve 124 and feed line 216. Culture medium 114 in supply bottle 115, in the case of this process, must completely or partly be replaced at more or less large intervals, preferably three times a week, via inlet 127 in order to prevent an accumulation of the harmful metabolites of the cultivated cells, as well as due to a large decrease of the nutrients. The hormone synthesized by the cells can then be obtained in a known manner by processing the culture medium. The flow-through-volume of the culture medium through the entire circulation system can be varied.

Figure 3:
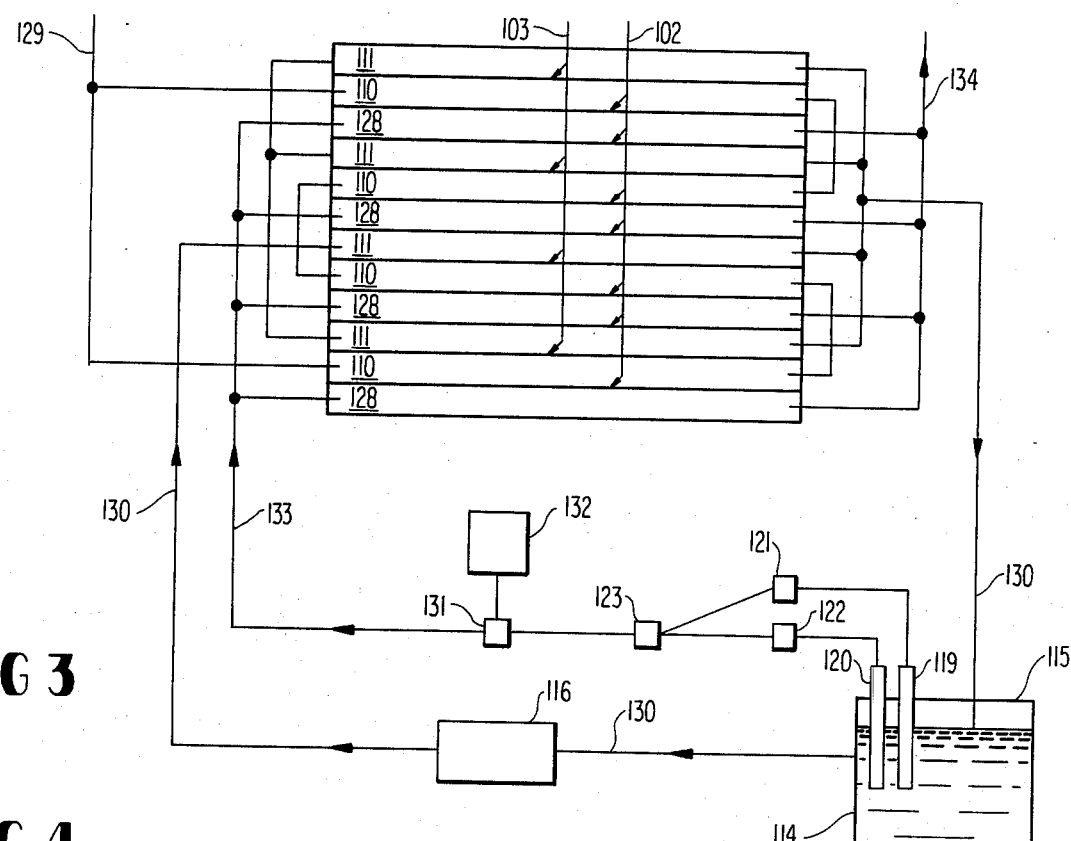
FIG. 3 is the functional pattern for the circulation process where the cell culture spaces are limited on the top by a culture medium space and on the bottom by a gas space.

The functional pattern to carry out the circulation process, where cell culture spaces 110 are each separated on top by a culture medium space 111 and below by a gas-space 128, is shown in FIG. 3. The cells are innoculated in suspension form into a suitable culture medium via inlet 129 and under asceptic conditions into cell culture space 110 of the sterile cell culture system. Cell culture space 110, at the same time, is separated on top by semipermeable flat membrane 103 from culture medium space 111 and below by a special gas-permeable-but-not-water-permeable flat membrane 102 from gas space 128. According to the process of this invention, preferably several layers of such arrangement are disposed on top of each other in the cell-culture system and in such a alternating way that one culture medium space 11, one cell culture space 110 and one gas space 128 form an alternating pattern. Gas space 128 is likewise separated from the culture medium likewise by a special gas-permeable-but-not-water-permeable flat membrane 102. Culture medium 114 is continuously conducted from supply tank 115 via pump 116 and inlet pipe 130 through culture medium space 111 of the cell culture system and back into supply tank 115. Supply tank 115 is equipped with measuring arrangements 119 and 120, in order to make pH and oxygen measurements with instruments 121 and 122, respectively. Instruments 121 and 122 are connected to control device 123 in order to control, via valve 131, a suitable gas mixture from tank 132 via inlet pipe 133 into gas space 128 of the cell culture system. The gas mixture flowing through gas space 128 is discharged from the cell culture system via line 134.

The process of this invention may also be carried out as a continuous flow-through process. The continuous flow through process is conducted basically in the same way, with the difference that in this case culture medium 114 is not returned to supply tank 115. The culture medium, after being conducted through the cell-culture system, can be used directly in a known manner for the isolation of the hormones.

The process of this invention makes it possible for the cultivated cells, which in the case of the use of the customary culture processes on solid surfaces, for example, glass or plastic, normally have a two dimensional growth, to multiply three dimensionally in the manner of a tissue on the semipermeable flat membranes. This striking effect rests upon continuously supplying the cultivated cells with nutrients, as well as upon continuously eliminating the poisonous metabolism products of the cells from the cell culture space by way of the two semipermeable flat membranes in (adjacent to) the culture-medium space. As a result of the use of semipermeable flat membranes of variable porosity and thickness, the exchange of material can be controlled in regard to volume and size in order to achieve an optimum supply and removal of supply of the cultivated cells (as well as an optimum separation of the synthetized hormone).

As a result of the fact that the cells cultivated according to this invention show a tissue-like three-dimensional growth, the requirement for mass cultivation has been fulfilled. Moreover, the addition of blood serum in the culture medium circulation may be reduced from a standard 5 to 10 percent to less than 0.5 percent.

Furthermore, the cells can be cultivated for several months without losing their specific synthesis function during this period of time. Contrary to the customarily used surface or suspension processes, the specific synthesis function of the cells cultivated with the process of this invention is higher by at least the factor 5, related to the same quantities of innoculated cells.

As used herein, all parts, ratios and percentages are on a weight basis unless otherwise stated herein or obvious to one ordinarily skilled in the art.

Figure 4:
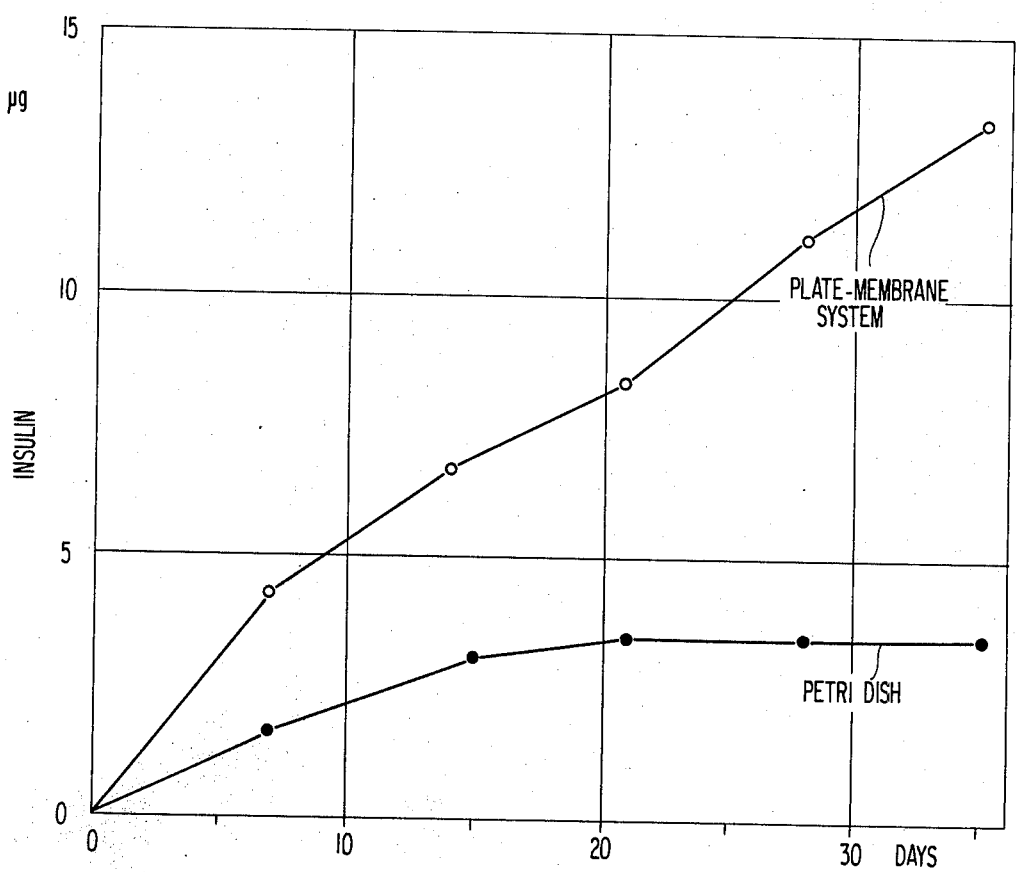
FIG. 4 is a graphical comparison of the insulin-synthesis function plate membrane system and the Petri dish where the cummulative values are calculated for $10^7$ cells.
Figure 5:
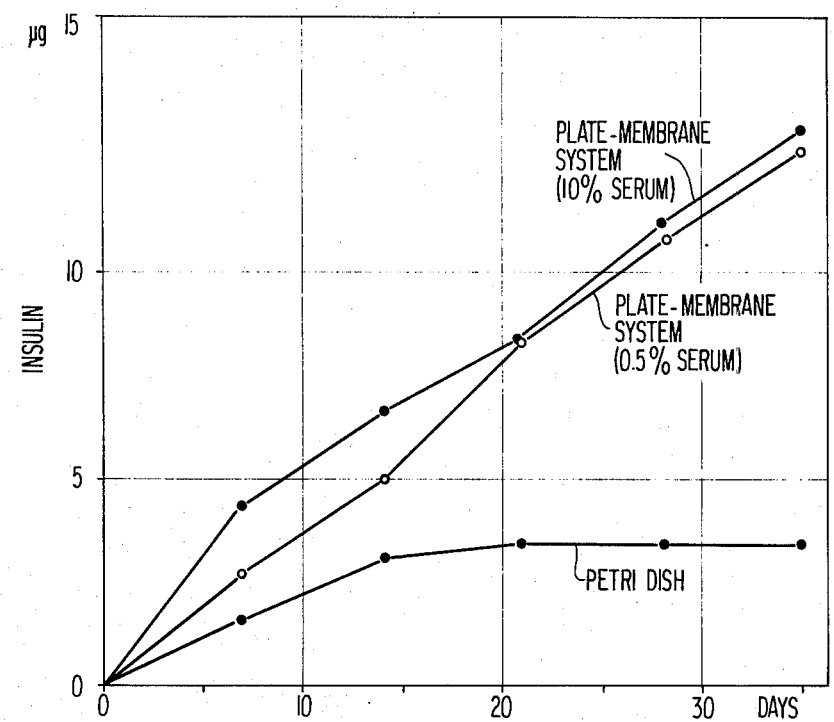
FIG. 5 is a graphical comparison of the insulin-synthesis function plate membrane system and the Petri dish with cummulative values.
Figure 6:
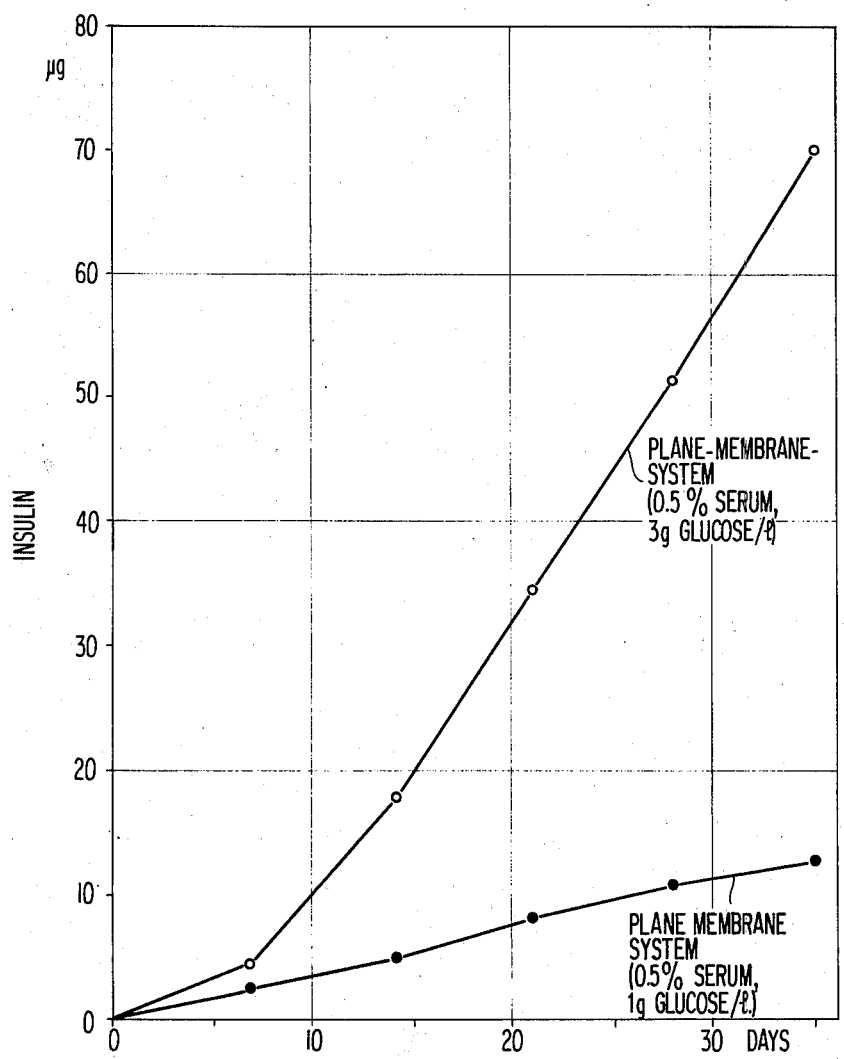
FIG. 6 is a graphical comparison of insulin synthesis in the plate membrane system with variable culture medium.

In the subsequent specific examples the process according to this invention is explained in more detail (reference is made therein to FIGS. 4 to 6).

EXAMPLE 1

(a) Production of the cells

The pancreata of 3 to 5 days old rats (of either sex of the strain Wistar) are removed after decapitation under aseptic conditions and collected in an ice-cold phosphate-buffered salt medium (pH 7.0) of the following composition:

NaCl: 8.0 g
KCl: 0.2 g
KH$_2$PO$_4$: 0.2 g
Na$_2$HPO$_4$: 1.15 g
glucose: 0.05 g
distilled water: 1000 ml The pancreata (in the medium) are subsequently (without any further communication) subjected directly to an enzyme treatment with a trypsin-collagenase solution having a pH value of 7.0 for the production of a pancreas-cell suspension. The total composition of the treating medium is:

NaCl: 8.0 g
KCl: 0.2 g
KH$_2$PO$_4$: 0.2 g
NaHPO$_4$: 1.115 g
glucose: 0.05 g
trypsin: 0.5 g
collagenase: 0.02 g
distilled water: 1000 ml For this purpose, dried, powdered trypsinenzyme, which is distributed by the firm Difco under the name of "Trypsin 1:250", and collagenase of the firm Worthington, is used.

For the enzyme treatment, 5 ml of enzyme solution is added to 30 to 40 pancreata is an Erlenmeyer flask. They are incubated for 15 mins. at 37° C. while stirring lightly with a magnetic stirrer. The supernatant is pipetted off after sedimentation of the little pieces of tissue and 5 ml of enzyme solution is added again. This process is repeated about 8 to 10 times until the tissue is completely digested. Any supernatant is immediately mixed with 5 ml of ice-cold culture medium and is kept in an ice bath until centrifugation. Medium 199 (modified) with Earle's salts, which is distributed by Flow Laboratories, is used as the culture medium. Additionally, 10 percent fetal calf serum from Flow Laboratories, as well as 4×10$^5$ IE penicillin G from Hoechst AG, per liter of medium are added to the culture medium. After centrifuging, the cells of the individual fractions are combined, washed once more with culture medium and finally re-suspended in the culture medium to a concentration of about 1 to 3×10$^7$ cells per milliliter.

(b) Cell-culture system

The cultivation of the cells is accomplished in a round plate-membrane system having a diameter of 38 mm. (which is shown schematically in FIG. 1) between the two tightened, transparent flat membranes of cellulose acetate. The molecular weight exclusion limit of the membranes used is about 80,000. The two culture medium spaces are closed to the outside by a glass pane in order to effect microscopic control of the cell growth. The distance between the two flat membranes is 2 mm and the cell growth surface to about 11.3 cm$^2$.

(c) Cell cultivation

The plate membrane system is sterilized with 4M rad, using a 60$_{Co}$-source, and is subsequently assembled as a circulation system. Silicon hose with an inside diameter of 1 mm is used for connecting the plate-membrane system with the supply bottle. All these parts are autoclaved at 1 bar for 30 min. After that 10$^7$ cells of the above produced innoculation agent are innoculated into the cell-culture space of the plate-membrane system. 100 ml culture medium are introduced under sterile conditions into the supply bottle. The entire circulation system is placed into a sheathed carbon dioxide incubator and is incubated at 37° C. An air mixture containing 5 percent carbon dioxide is continuously introduced into the incubator. The connecting hoses (made of silicon rubber) serve in this case as an oxygenator for the culture medium, since the connecting hoses are very easily gas permeable. After that the hose pump is turned on, whereby the culture medium is pumped continuously at a flow velocity of 2 ml/min through the two culture medium spaces of the plate-membrane system and returned to the supply bottle. The entire culture medium in the supply bottle is completely replaced every 3 or 4 days by new culture medium.

As a control, always 5×10$^6$ cells of the above produced innoculation agent are incubated under corresponding conditions in plastic Petri dishes having a diameter of 50 mm in 5 ml of the above used culture medium. This corresponds to the normally used monolayer process for the cultivation of cells. In this case too, the culture medium is completely replaced every 3 or 4 days. Always the drawn off culture medium is collected separately, and kept back for the determination of the insulin content, in order to obtain a statement about the insulin-synthesis function of the cells. The determination of the insulin content is accomplished with the use of a radioimmuno assay for insulin (from the firm Novo, of Copenhagen), whereby rat insulin is used as the standard.

The incubation of the cells takes place over 35 days. The cells cultivated in the plate-membrane system show a three-dimensional tissue-like growth during the entire experimental time. In the Petri dishes, to the contrary, there is two dimensional growth. The result for the insulin synthesis function of the cells thus-cultivated is shown in FIG. 4, wherein cumulative curves of the insulin contents in the culture medium are given (the insulin values being calculated for equal numbers of innoculated cells). The advantage of the plate membrane systems can be readily seen on the basis of considerably higher insulin values.

EXAMPLE 2

The general procedure of Example 1 is repeated, with the exception that the culture medium used in the culture medium space has an addition of only 0.5 percent of serum (contrary to Example 1 with the use of a culture medium with an addition of the customary 10 percent). For the controls in Petri dishes, again a culture medium with an addition of 10 percent serum is used. The incubation of the cells takes place over 35 days. The cell growth shows the same pattern as the one described in Example 1. The result for the insulin biosynthesis function of the cells cultivated thus is shown in FIG. 5 (corresponding to the manner described in Example 1). Additionally, the cumulative curve of the experiment, described in Example 1, is also shown. From the curves one can see that a reduction of the serum content in the medium of the culture medium space from the customary 10 percent to 0.5 percent has no negative influence on the insulin-synthesis function of the cells cultivated in plate membrane systems, but instead leads to a considerable reduction of the cost for the medium.

EXAMPLE 3

The general procedure of Example 1 is repeated, with the exception that the material used in the culture medium space has an addition of 0.5 percent serum. Furthermore, the glucose content is increased from the normal 1 g/l to 3 g/l. It is well known that the insulin synthesis function of the cells may be stimulated by increasing the glucose content. The incubation of the cells takes place over 35 days. The cell growth shows the same picture as described in Example 1. The result for the insulin synthesis functions of the cells thus-cultivated is shown in the manner described in Example 1. Additionally, the cumulative curve of the experiment described in Example 2 is shown. From FIG. 6 one can see that the insulin synthesis function of the cells is increased by an increase of the glucose content in the culture medium and thus the insulin yield can be considerably increased.

What is claimed is:

1. Process for the in-vitro biosynthesis of a hormone comprising the steps of (a) introducing (i) cells from organs or tissues of animal or human origin into one or more cell culture spaces and (ii) culture medium separately into one or more culture medium spaces, each cell culture space having a flat top and flat bottom, each culture medium space having a flat top and a flat bottom, when more than one culture medium space and more than one cell culture space are used, the culture medium spaces are in alternating relationship to the cell culture spaces, the culture medium spaces are adjacent to the cell culture spaces, and a culture medium space is located on top of each cell culture space, when one culture medium space and one cell culture space are present, the culture medium space is located adjacent to and on top of the cell culture space, and each culture medium space is separated from each adjacent cell culture space or spaces by a semi-permeable flat membrane which is permeable to liquid and is impermeable to cells, (b) propogating or cultivating in vitro the cells under suitable cell growth or cell cultivation conditions, respectively, whereby the cells in vitro biosynthesize the hormone, and (c) isolating the resultant hormone from the culture medium and/or by processing the cells after removing the cells from the cell culture space.

2. Process as claimed in claim 1 wherein the culture medium is in a circulation system and is repeatedly conducted into the culture medium space, the circulation system having a culture medium supply container, measurement and control equipment and optionally an oxygenator.

3. Process as claimed in claim 1 wherein the culture medium, in a continuous flowthrough system, is conducted once into the culture medium spaces in order to obtain the substances released via the membranes.

4. Process as claimed in claim 1 wherein, when more than one culture medium space and more than one cell culture space are used, each cell culture space is separated from the culture medium spaces by semipermeable flat membranes located on top of and below each such cell culture space.

5. Process as claimed in claim 1 wherein the cell culture spaces are separated by semipermeable flat membranes on top from a culture medium space and below from a gas space.

6. Process as claimed in claim 1 wherein the semipermeable flat membranes are permeable to molecules having a molecular weight of up to 100,000.

7. Process as claimed in claim 1 wherein the semipermeable flat membranes have a thickness of 10 to 150 μm.

8. Process as claimed in claim 1 wherein the semipermeable flat membranes are made of cellulose, a cellulose derivative, a polypeptide, a polyamide, a polysulfone or a polyacrylic nitrile.

9. Process as claimed in claim 1 wherein the hormone that is biosynthesized in vitro is insulin.

10. Process as claimed in claim 1 wherein the thickness of each semipermeable flat membrane is from 30 to 100 μm.

11. Process as claimed in claim 1 wherein the distance between the semipermeable flat membranes is 2 mm.

12. Process as claimed in claim 1 wherein, added blood serum is present in the culture medium in the culture medium in the culture medium spaces in an amount of 0.5 percent by weight for less based on the weight of the culture medium in the culture medium spaces.

* * * * *